(12) United States Patent
Faber et al.

(10) Patent No.: US 6,344,173 B1
(45) Date of Patent: *Feb. 5, 2002

(54) AUTOMOTIVE HYDROCARBON SENSOR

(75) Inventors: Margaret K. Faber, Corning; Yuming Xie, Painted Post; Zhigang Zhou, Corning, all of NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/451,075

(22) Filed: Nov. 30, 1999

Related U.S. Application Data

(60) Provisional application No. 60/111,191, filed on Dec. 7, 1998.

(51) Int. Cl.$^7$ .............................................. H01N 31/12
(52) U.S. Cl. ........................... 422/94; 422/98; 436/143; 436/137
(58) Field of Search ................................ 436/143, 137; 422/95, 94, 99

(56) References Cited

U.S. PATENT DOCUMENTS

| | | |
|---|---|---|
| 2,980,743 A | 4/1961 | Toft |
| 3,560,160 A | 2/1971 | Lanneau |
| 3,898,181 A | 8/1975 | Barker |
| 3,906,721 A | 9/1975 | Micheli et al. |
| 3,914,376 A | 10/1975 | Barker |
| 4,006,103 A | 2/1977 | Meguerian et al. |
| 4,012,485 A | 3/1977 | Meguerian et al. |
| 4,036,592 A | 7/1977 | Brown et al. |
| 4,128,506 A | 12/1978 | Hegedus et al. |
| 4,171,287 A | 10/1979 | Keith |
| 4,256,985 A | 3/1981 | Goodson et al. |
| 4,289,737 A | 9/1981 | Acres et al. |
| 4,624,940 A | 11/1986 | Wan et al. |
| 4,863,691 A | 9/1989 | Noguchi et al. |
| 4,975,406 A | 12/1990 | Frestad et al. |
| 4,976,929 A | 12/1990 | Cornelison et al. |
| 5,157,204 A | 10/1992 | Brown et al. |
| 5,177,464 A | 1/1993 | Hamburg |
| 5,255,511 A | 10/1993 | Maus et al. |
| 5,265,417 A | 11/1993 | Visser et al. |
| 5,314,828 A | 5/1994 | Dalla Betta et al. |
| 5,408,215 A | 4/1995 | Hamburg |
| 5,444,974 A | 8/1995 | Beck et al. |
| 5,472,580 A | 12/1995 | Kennard, III et al. |
| 5,476,001 A | 12/1995 | Hoetzel et al. |

(List continued on next page.)

FOREIGN PATENT DOCUMENTS

| | | |
|---|---|---|
| EP | 0 358 925 | 3/1990 |
| EP | 0 751 390 | 1/1997 |
| JP | 59-0058116 | 4/1984 |

*Primary Examiner*—Jill Warden
*Assistant Examiner*—Samuel P. Siefke
(74) *Attorney, Agent, or Firm*—Timothy M. Schaeberle; Kees van der Sterre

(57) ABSTRACT

A sensor for measuring the non-methane HC concentration of gas sample, e.g., automotive exhaust gas, the sensor comprises a sensor base, capable of producing a output signal representative of the exothermic effect of the hydrocarbon species in the gas sample. The sensor base has disposed on, and integral with, its surface, a porous selective oxidation catalyst layer comprising capable of selectively oxidizing a combination of $CO+H_2+$alkene species in the gas sample and leaving unoxidized the alkane and aromatic hydrocarbons. The sensor base further includes a first supported resistance temperature device which has disposed thereon a total oxidation catalyst layer capable of oxidizing the remaining alkane and aromatic hydrocarbon species in the gas sample, and a non-catalyzed second resistance temperature device.

6 Claims, 2 Drawing Sheets

U.S. PATENT DOCUMENTS

| | | |
|---|---|---|
| 5,486,336 A | 1/1996 | Dalla Betta et al. |
| 5,494,701 A | 2/1996 | Clough et al. |
| 5,494,826 A | 2/1996 | Stetter et al. |
| 5,517,848 A | 5/1996 | Hosoya et al. |
| 5,560,200 A | 10/1996 | Maus et al. |
| 5,597,772 A | 1/1997 | McCabe et al. |
| 5,687,565 A | 11/1997 | Modica et al. |
| 5,689,059 A | 11/1997 | Oh et al. |
| 5,795,545 A | 8/1998 | Koripella et al. |
| 5,798,270 A | 8/1998 | Adamczyk et al. |
| 5,813,764 A * | 9/1998 | Vissor et al. ............. 374/12 |
| 5,858,306 A | 1/1999 | Oh et al. |
| 6,037,183 A * | 3/2000 | Faber et al. ............. 436/137 |

\* cited by examiner

AUTOMOTIVE HYDROCARBON SENSOR

This application claims the benefit of U.S. Provisional Application No. 60/111,191, filed Dec. 7, 1998, entitled "Automotive Hydrocarbon Sensor", by Faber et al.

BACKGROUND OF THE INVENTION

1. Field of the Invention

The present invention relates generally to the technology of measuring the non-methane hydrocarbon concentration in the emissions of an automotive internal combustion engine, and more particularly to the use of a catalytic differential calorimetric sensor, having a thin film selective catalyst layer, to monitor the non-methane oxidation efficiency of an exhaust system's catalytic converter.

2. Description of the Related Art

Catalytic converters have been used on gasoline-fueled automobiles produced in the United States since the mid-1970's for the purpose of promoting the oxidation of unburned hydrocarbons (HCs) and of carbon monoxide (CO). Soon after their introduction, the converters were adapted to promote the chemical reduction of oxides of nitrogen ($NO_x$). At the present time these converters typically employ small amounts of platinum, palladium and rhodium dispersed over a high surface area particulate carrier vehicle which, in turn, is distributed as a thin, porous coating (sometimes called a washcoat) on the wall of a ceramic monolith substrate. The substrate is typically formed by an extrusion process providing hundreds of thin wall, longitudinal parallel open cells per square inch of cross section. These flow-through catalytic devices are housed in a suitable stainless steel container and placed in the exhaust stream under the vehicle downstream from the engine's exhaust manifold.

Under warm, steady-state engine conditions, this conventional catalytic converter containing the precious metal based three-way catalyst (TWC), so called because it simultaneously affects the oxidation of CO and unburned HC's and the reduction of $NO_x$, effectively and efficiently removes most of the automotive emissions. However, the catalyst system may become malfunctioning after experiencing thermal aging at an unusually high temperature, due to high exposure to poisoning gases like $SO_2$, Si and Pb, etc. Furthermore, new emissions regulations require an extended durability of the catalytic converter from 50,000 miles to 100,000 miles. The California Air Resource Board (CARB), has recently enacted the On-Board Diagnostics-II (OBD-II) regulation which ensures that vehicles meet the certified emission standards throughout the vehicle's operation life. Specifically, the regulation requires that any monitoring system should be able to indicate when the catalyst system is malfunctioning and its conversion capability has decreased to the point where either of the following occurs: (1) HC emissions exceed the applicable emission threshold of 1.5 times the applicable Federal Test Procedure (FTP) HC standard for the vehicle; and (2) the average FTP Non-methane Hydrocarbon (NMHC) conversion efficiency of the monitored portion of the catalyst system falls below 50 percent.

Automotive emissions prior to the catalyst system reaching its operational temperature, namely, cold start emissions, make up the majority of pollution from automobiles. Various approaches for reducing these emissions have been shown to be effective, including, for example, close-coupled catalytic converters, electrically heated catalytic converters and in-line adsorbers which temporarily store unburned hydrocarbons until the catalytic converter lights off. Again, OBD-II regulations require that systems be installed in the exhaust system to directly monitor the functional status of any of these "cold-start" devices during the lifetime of the car (100,000 miles).

A direct result of this OBD-II legislation, is that the use of gas sensors, namely hydrocarbon sensors, for use as on-board catalytic efficiency monitors, although technologically new, has gained increasing popularity in the auto industry. Generally, the use of a catalytic calorimetric sensor, which measures the effect of the exotherm of the catalyzed oxidation of the hydrocarbons over supported precious metal catalysts on the resistance of a coil conductor is known.

U.S. Pat. No. 5,444,974 (Beck et al.) discloses a method of diagnosing the performance of the catalytic converter for the oxidation of CO and HC involving producing an electrical signal from a calorimetric sensor located in the exhaust stream downstream of the catalytic converter. The calorimetric sensor is comprised of a first portion bearing an oxidized catalyst for CO, $H_2$ and HC and an adjacent second portion that is oxidation catalyst-free.

A shortcoming of Beck, a reduced ability to accurately measure the HC concentration, is due to the fact that it does not compensate or account for the interference of CO, the concentration of which is typically an order of magnitude or greater than the concentration of the HC species.

U.S. patent application Ser. No. 08/980,925 (Faber et al.), a recent innovation, describes a system for measuring the non-methane HC concentration of automotive exhaust gas, that overcomes this sensitivity problem. The Faber system includes a selective sensor catalyst having an oxidation catalyst capable of selectively oxidizing the combination of $CO+H_2$+alkene hydrocarbons and a catalytic differential calorimetric sensor, located downstream of the sensor catalyst, that is capable of producing a output signal representative of the exothennic effect of the remaining aromatic and alkane hydrocarbons species in the exhaust gas sample. This output signal is analyzed and converted into measure that is representative of the concentration of the total non-methane hydrocarbon species.

Although the system of Faber represents an improvement over those calorimetric sensors of the prior art, the systems disclosed therein are unnecessarily complex in their design. As such, there still exists a need for a simpler system for measuring the non-methane HC concentration.

SUMMARY OF THE INVENTION

Accordingly, the present invention is directed at a sensor having a simpler design for selectively and directly measuring the non-methane hydrocarbon concentration in a gas sample; e.g., the exhaust gases produced by an internal combustion engine. This simple hydrocarbon sensor is capable of detecting, under a variety of engine and fuel conditions, including cold start conditions, low (ppm) concentrations of non-methane hydrocarbons in exhaust gases, containing a variety of gaseous components, in addition to hydrocarbons.

Simply stated, the sensor has the capability of selectively oxidizing the combination of $CO+H_2$+alkene hydrocarbons in a gas sample prior to measurement. Specifically, the sensor is provided with a porous, thin film oxidation catalyst layer capable of selectively oxidizing $CO+H_2$+alkene hydrocarbon combination while leaving the aromatic and alkane hydrocarbons unoxidized. The sensor is further provided with a sensor base having, supported thereon or embedded therein, a pair of resistance temperature devices which are collectively capable of producing a signal representative of the concentration of unoxidized aromatic and alkane hydrocarbons in the exhaust gas to thereby enable the determination of the concentration of the total non-methane hydrocarbon species.

DETAILED DESCRIPTION OF THE INVENTION

The present invention is directed at a system for measuring the hydrocarbon concentration of a gas sample. In its simplest embodiment, the sensor comprises a sensor base having a pair of resistance temperature devices capable of generating an output signal representative of the exothermic effect of the hydrocarbon oxidation that contact it. The sensor base has disposed on its surface, a thin film porous oxidation catalyst layer capable of selectively oxidizing a combination of $CO+H_2$+alkene species in the gas sample and leaving the alkane and aromatic hydrocarbons unoxidized. Simply stated, the sensor RTDs combination signal is representative of the oxidation of the remaining oxidizable species in the gas sample; i.e., the alkane and aromatic hydrocarbons. Specifically, the pair of resistance temperature devices, one having a total oxidation catalyst layer, are capable of providing data to indicate the concentration of unoxidized aromatic and alkane hydrocarbons in the gas sample; which directly correlates to the total non-methane hydrocarbon concentration. Furthermore, the RTDs are capable of maintaining the total oxidation layer and thin film porous catalyst layer at a sufficient temperature to ensure the respective oxidations each is subject to.

Figure 1:
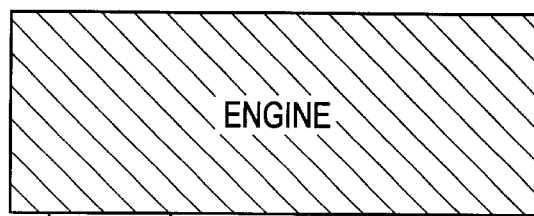
FIG. 1 is a schematic diagram of an embodiment of the positioning of the sensor for measuring hydrocarbon concentration of an exhaust gas stream.

Referring to FIG. 1, illustrated therein is a simple schematic representation of the sensor 10 for measuring hydrocarbon concentration of exhaust gases in an exhaust stream, according to one embodiment of the present invention. A main catalytic converter 12 is located in the exhaust gas downstream of an internal combustion engine. This main catalytic converter 12 is capable of catalyzing the exhaust gas so as to reduce the pollutants present in the exhaust gas. Preferably, the catalyst is a three-way catalyst which functions to oxidize both HCs and CO, as well as to reduce $NO_x$, in the exhaust gas. The sensor 10, generally comprises a sensor base 14 and a porous thin film selective oxidation catalyst layer 16 that is disposed on, and is integral with the catalyst sensor portion 14. The sensor is located within the exhaust stream to directly measure the non-methane hydrocarbon concentration in the exhaust gas, with the sensor preferably positioned in a manner such that the porous thin film selective oxidation catalyst is maintained perpendicular to the flow of the exhaust gas. Hydrocarbons as oxidized/ measured and referred to herein, refer to non-methane hydrocarbons (HC).

In a separate embodiment, the sensor could be located upstream of the main converter whereby the measurement would be of the concentration of an upstream portion of exhaust gas.

Figure 2:
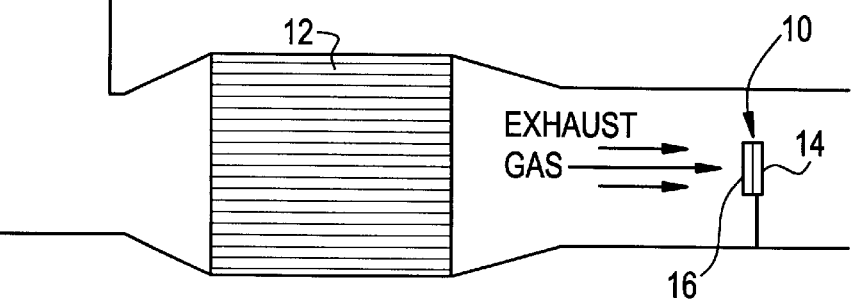
FIG. 2 is a schematic illustration of an additional off-line positioning of the inventive sensor for measuring hydrocarbon concentration.

Referring now to FIG. 2 illustrated therein is an alternative off-line positioning of the hydrocarbon sensor. Specifically, the sensor 10 is located in a bypass channel 18 having an entrance 20 and exit 22 connected to the housing 24 of the main exhaust flow. It is contemplated that this off-line measurement system could be configured such that the exhaust gas once measured is released into the atmosphere; the analyzed gas having been catalyzed so as to be non-harmful.

Figure 3:
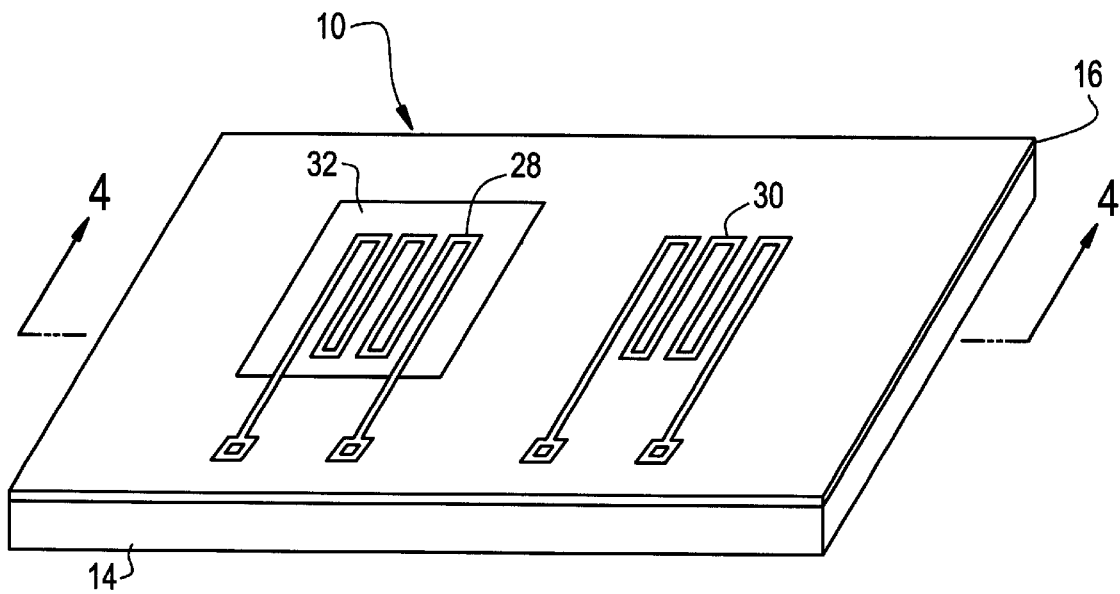
FIG. 3 is a schematic diagram of the sensor for measuring hydrocarbon concentration of an exhaust gas stream, according to the invention described herein.
Figure 4:
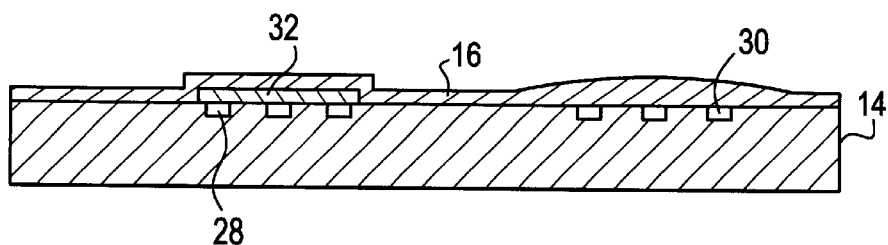
FIG. 4 is a cross-section of FIG. 3 taken along lines 4—4.

Referring to FIGS. 3 and 4, illustrated therein is an embodiment of the schematic the sensor 10 according to the instant invention. The sensor 10, comprises sensor base 14 upon which is supported two resistance temperature devices (RTD) 28 and 30; either directly on the surface of, or within, the sensor base. A total oxidation catalyst layer 32 covers the first RTD 28, while the second RTD 30 remains uncovered. Sensor further includes, disposed on top of the sensor base 14, a thin film, porous selective oxidation catalyst layer 16. The thin film, porous selective oxidation catalyst layer 16, is comprised of a porous catalyst support material having impregnated within the pores, a catalytically active precious metal capable of selectively oxidizing a combination of $CO+H_2$+alkene species and leaving unoxidized the alkane and aromatic hydrocarbons.

The thickness of the selective oxidation layer 16 is generally uniform across the sensor base 14, except for that portion of the selective oxidation layer which is disposed on the second RTD 30, which is of a thickness substantially equal to the combined thickness of the oxidation layers that cover the first RTD 28, specifically the combination of the oxidation layer and the total oxidation catalyst layer. A configuration wherein the thickness provided on each of the RTDs is substantially equivalent ensures that the gases travel through an equivalent catalytic layer amount. Furthermore, in the configuration as described above, the selective catalyzing that occurs proximate to the second RTD, in the thicker selective catalyst layer, occurs in the surface portion of the selective layer while the portion of the selective layer nearer the sensor base remains essentially inert. This near surface catalyzation ensures that the thermal effect on each of the RTDs due to the oxidation by the selective layer is essentially equivalent. In other words, in the configuration above, the selective oxidation occurs at approximately the same distance for each of the respective first and second RTDs.

One additional principle regarding the thickness of the selective oxidation layer 16 is that this layer should be of a dimension such that it is thin enough to allow most of the exhaust gas to diffuse through, yet should be thick enough to be capable of substantially selectively oxidizing the combination of $CO+H_2$+alkene species in the exhaust gas.

Referring specifically to RTDs 28 and 30, resistance temperature device 28 is covered by an total oxidation catalyst layer 32 comprising a catalyst-support material and a catalytically active precious metal capable of oxidizing the oxidizable species that remain unoxidized, while the second resistance temperature device 30 does not contain this total oxidation catalyst layer and functions as a reference.

The sensor base 14 is configured to be as thin as possible and is comprised of a dielectric material with a high heat conductivity, preferably a ceramic material, including for example, aluminum oxide, silicon oxide or silicon nitride.

RTDs 28 and 30 are typically made of a sputtered platinum film patterned by lithography and a chemical etch.

Briefly the sensor functions in the following manner. The exhaust gas diffuses through the thin film, porous selective oxidation catalyst layer 16 and contacts the selective catalytic precious metal material which selectively oxidizes the $CO+H_2$+alkene species present in the exhaust gas portion. The exhaust gas, still containing unoxidized alkane and aromatic HCs, thereafter comes in contact with the total oxidation catalyst layer which oxidizes the remaining oxidizable species present in the exhaust gas, the alkane and aromatic hydrocarbons. The resultant oxidation reaction causes a temperature increase $-T=$[alkane+aromatic HCs] in the first RTD, above that of the RTD without the total oxidation catalyst layer, the difference is thereafter used for producing a signal representative of this exothermic effect. Put differently, oxidation of the remaining oxidizable species (alkane and aromatic HC), an exothermic reaction in which energy is released, will raise the temperature of the first RTD 28 above that of the second reference RTD 30.

In a preferred embodiment the RTDs could be heated to a set temperature by passing currents through the RTDs 28 and 30. Specifically, each of the RTDs would be operated by heating the RTD to a set temperature by passing the current to each and thereafter measuring the difference in required current necessary to maintain the set temperature of the oxidation and reference RTD. This difference would be a measure of the oxidation exotherm occurring as result of oxidation by the total oxidation layer and could be analyzed to determine the amount of the HC's present in the exhaust. In this embodiment the heated RTDs 28 and 30 would thus perform the dual functions of the measurement of the temperature increase and the maintaining of the total catalyst layer and the porous catalyst layer at a constant, elevated temperature, sufficient to ensure that the catalytic oxidation process occurs, i.e., substantially complete oxidation of any oxidizable species.

In an alternative embodiment, the RTDs could be a part of a Wheatstone bridge, in which case, the comparison between the RTD outputs is directly proportional to the amount of the HC's present in the exhaust gas. In this embodiment a separate heater would be needed to maintain the total and selective oxidation catalyst layers at a constant, elevated temperature, which would be sufficient to ensure that the catalytic oxidation process occurs.

The measured temperatures are converted to an electrically measurable quantity, resistance, or heating current, in the case of the RTDs and thereafter analyzed to calculate the aromatic and alkane hydrocarbon concentration and thus the total hydrocarbon concentration. It is contemplated that a microprocessor based electronic control unit (ECU) can be used as to analyze the measurable temperature outputs to generate the output signal of the catalytic differential calorimetric sensor. The ECU would thereafter analyze the exotherm to indicate the aromatic and alkane concentration and thereafter the total concentration of unburned hydrocarbons in the downstream exhaust gas.

Figure 5:
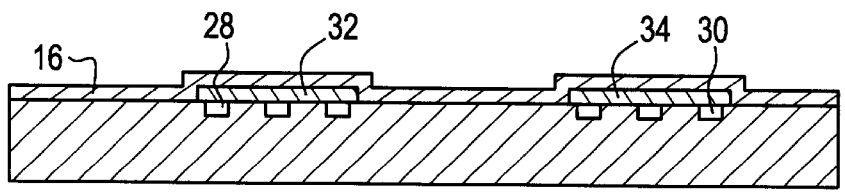
FIG. 5 is a cross-section of an alternative embodiment of the sensor of FIG. 3 taken along lines 4—4.

Referring now to FIG. 5, illustrated is a second embodiment of the sensor of FIG. 3. In a second embodiment, the sensor base 16 would include an identical first total oxidation catalyst layer covering the first RTD 28, however, the second RTD 30 would include a non-catalytic layer 34 of the same thickness as the total oxidation catalyst layer. This non-catalytic layer would be comprised of a high surface area catalyst support material comprising either $SiO_2$ or $Al_2O_3$ or any non catalytically active material that possessed substantially the same thermal conductivity as the catalyst support material utilized for the total oxidation catalyst layer. As in the first embodiment, this second non-catalytic layer would ensure that the exhaust gas that passes through the porous thin film selective oxidation layer and contacts each of the two respective RTDs 28 and 30 would be subject to the equivalent amount of selective oxidation and would occur at the approximately the same distance from the RTDs, thereby ensuring a more accurate measure of the non-methane HC concentration.

It is contemplated that the proper configuration of the sensor, for example, the thickness of the selective catalyst layer, should be empirically determined to ascertain which configuration will ensure a sensor possessing a sufficient level of sensitivity; i.e., a configuration that performs well under cold start conditions may not sufficiently perform under warm steady-state conditions. Furthermore, under certain conditions it may be preferable to include an amplification means so that the signal of the sensor is detectable.

As described above, the thin film porous selective oxidation catalyst layer comprises a catalyst-support material and the appropriate catalytically active precious metal impregnated within the pores of the catalyst support material. Preferably, the thin film porous layer exhibits a thickness of between about 0.1 to 10 $\mu$m.

As indicated above it is essential that the catalyst support material has impregnated within its pores, a catalytically active precious metal that selectively oxidizes the $CO+H_2$+alkene HC combination. One such selective catalytically active precious metal comprises an amount of highly dispersed Rh-cluster deposits supported on the high surface area catalyst-support material, preferably silica. The selective catalytically active precious metal according to the invention should be prepared in accordance with a method that ensures that the Rh-cluster deposits supported on the high surface area catalyst-support material are highly dispersed. Specifically, "highly-dispersed" as used herein, refers to Rh-cluster deposits covering no greater than about 10% of the surface area of the support material, preferably no greater than about 5% of the surface area of the support material. Furthermore, the method of preparation should ensure that the Rh-cluster deposits exhibit the proper size, as deposited on the surface catalyst-support material. The Rh-cluster deposits, comprised of a single rhodium atom or a cluster of at least two Rh atoms should exhibit a diameter of less than about 5 nm, preferably less than about 1 nm, most preferably less than about 5 Å. If the Rh-deposits are too closely spaced together they will effectively function as if a precious metal layer is deposited on the support material surface, the result being a loss of the selective oxidation feature which is obtained as a result of the small size and high dispersion of the Rh-deposits.

In addition to the aforementioned limitation on the surface area coverage of the Rh-cluster deposits, which exhibit a hemispherical-like shape on the catalyst support surface, it is critical that the total amount of rhodium comprise an amount on the catalytic-support material, which will be sufficient to provide a small but catalytically effective amount of the rhodium metal to substantially and completely catalyze the $CO+H_2$+alkene HCs in an exhaust gas portion. For example, the total amount of Rh which should be deposited on a catalyst-support having an approximate area of 150 $m^2/g$, should be less than about 0.3%, by weight, of the total support and precious metal weight, and preferably, less than about 0.1%, by weight of the total weight. This small amount of Rh loading ensures that the Rh clusters remain highly dispersed and thus the Rh-containing catalyst remains highly selective.

In this thin-film selective oxidation layer the precious metal rhodium component is the main catalytically active component in the catalytic reaction, and it is the principal aim of the highly dispersed and small sized rhodium to selectively oxidize the CO+$H_2$+alkene HC species. While not intending to be limited by the theory it is thought that the selective nature of the thin-film porous oxidation catalyst layer is based on a combination of the highly dispersed nature and small size of the rhodium clusters that are deposited on the surface of the catalytic-support material.

Suitable materials for use as the porous thin film layer catalyst support material includes high surface area materials, preferably a ceramic material, selected from the group consisting of silica, $\gamma$-$Al_2O_3$, $ZrO_2$, Al-Mg spinel $SiO_2$, $TiO_2$ and mixtures thereof. For the following reasons, silica comprises the preferable catalyst-support material: (1) silica ($SiO_2$) is more acidic and thus exhibits a reduced affinity, when compared to alumina, titania and zirconia, for attracting the $SO_2$ molecule, therefore reducing $SO_2$ concentration over the $SiO_2$ surface which directly results in less contact of $SO_2$ with the active Rh site (poisoning); (2) silica exhibits a greater static reaction effect, thus resulting in a greater ability to hold the Rh-cluster deposits in highly dispersed states. Alumina and titania are suitable for use as the catalytic support material, however, they have a stronger interaction with $SO_2$, thus $SO_2$ has a more profound poisoning effect on the catalytic activity. As such, an alumina or titania supported Rh-catalyst would require a higher operating temperature thus resulting in a smaller "window" for oxidation to occur before the HCs begin to self ignite; as compared to a catalytic "window" for the preferred catalytic-support material, silica".

A suitable procedure for preparing the Rh-containing catalyst, so as to ensure high dispersion, small sized Rh-cluster deposits on the surface of the catalytic-support material, in accord with the present invention generally involves the following steps: (1) adding Rh-containing compound (e.g., rhodium chloride) to a solvent (e.g., $H_2O$) to form a Rh-containing solution and thereafter adding an adequate amount of an ammonium-containing solution (e.g. $NH_4OH$) to form an Rh-ammonium solution; (2) impregnating an amount of a high surface area catalyst-support material powder with the Rh-ammonium solution by incipient wetness impregnation and thereafter drying and calcining this impregnated powder to form a dry powder mixture comprised of the high surface area catalytic-support material with highly dispersed Rh-deposits located on the surface. This dry powder mixture is applied to the surface of the sensor base through the use of a standard washcoating process; the particulars of which are within the knowledge of one skilled in the art.

A variety of Rh-containing compounds may be used in the above procedure including the nitrates, halides, acetonulacetonates or appropriate rhodium carbonyls; in other words any rhodium-containing material can be used as long as the result is small sized, highly dispersed Rh-cluster deposits.

Regarding the total oxidation catalyst layer, like that for the selective oxidation catalyst, it includes a precious metal supported on a catalyst support material. Any catalytically active precious metal which is capable of oxidizing alkane and aromatic HC's, i.e., the remaining oxidizable species, present in the exhaust gas portion would be suitable for use in the oxidation catalyst of the sensor. Suitable precious metals include rhodium, platinum, palladium, iridium, silver, gold, ruthenium, osmium, and mixtures thereof. As before, the suitable catalyst-support materials include any high surface area material, preferably a ceramic material, including for example, silica, alumina, titania, zirconia, ceria and mixtures thereof. It is preferred that the catalyst-support material of the sensor base be comprised of a ceria-containing material, more preferably ceria-zirconia solid solution.

In a preferred embodiment, the total oxidation catalyst layer 32 comprises platinum, palladium or a mixture thereof, supported by the aforementioned ceria-zirconia solid-solution catalyst-support material.

Although the now preferred embodiments of the invention have been set forth, it will be apparent to those skilled in the art that various changes and modifications may be made thereto without departing from the spirit and scope of the invention as set forth in the following claims.

We claim:

1. A sensor for measuring the hydrocarbon concentration of a CO+H2+hydrocarbon containing gas sample, comprising:

a sensor base, capable of producing a output signal representative of the exothermic effect of the hydrocarbon species in the gas sample, the sensor base having disposed on, and integral with, its surface a porous selective oxidation catalyst layer capable of selectively oxidizing a combination of CO+H2+alkene species in the gas sample and leaving unoxidized the alkane and aromatic hydrocarbons;

the sensor base further comprising a first supported resistance temperature device, having disposed thereon a total oxidation catalyst layer capable of oxidizing the remaining alkane and aromatic hydrocarbon species in the gas sample and comprising a high surface area catalyst-support material and a precious metal material supported thereon, and a non-catalyzed second resistance temperature device;

the porous selective oxidation catalyst layer being comprised of a high surface area silica catalyst-support material having a thickness of 0.1 to 10 $\mu$m with a precious metal comprising rhodium in the form of highly dispersed rhodium cluster deposits being disposed on the silica catalyst-support material, the rhodium cluster deposits comprising a single rhodium atom or a cluster of at least two rhodium atoms having a diameter of less than about 5 nm and covering no greater than about 10% of the surface area of the catalyst-support material.

2. The sensor of claim 1 wherein the rhodium cluster deposits exhibit a diameter of less than about 5 Å.

3. The sensor of claim 1 wherein the high surface area catalyst support material of the total oxidation catalyst layer is comprised of a material selected from the group consisting of alumina, titania, zirconia, silica, ceria and mixtures thereof.

4. The sensor of claim 1 wherein the precious metal of total oxidation catalyst layer is selected from the group consisting of rhodium, platinum, palladium, iridium, silver, gold, ruthenium, osmium, and mixtures thereof.

5. The sensor of claim 4 wherein the total oxidation catalyst layer comprises a ceria/zirconia solid solution catalyst-support material and a precious metal of platinum.

6. A sensor for measuring the hydrocarbon concentration of a CO+H2+hydrocarbon containing gas sample comprising:

a sensor base;

a pair of resistance temperature devices disposed on the surface of the sensor base, said pair including a first resistance temperature device covered by a total oxidation catalyst layer and a second resistance temperature device not covered by a total oxidation catalyst layer;

a porous, thin-film selective oxidation catalyst layer disposed on the sensor base covering the total oxidation catalyst layer and the first and second resistance temperature devices, the selective oxidation catalyst layer being comprised of a porous catalyst support material having impregnated within the pores a catalytically active precious metal capable of selectively oxidizing a combination of CO+H2+alkene species present in the gas sample while leaving unoxidized alkane and aromatic hydrocarbons present in the gas sample;

the selective oxidation layer having a thickness permitting the diffusion of the hydrocarbon-containing gas sample therethrough while substantially selectively oxidizing the combination of CO+H2+alkene species in the sample, and the total oxidation catalyst layer being effective to oxidize alkane and aromatic hydrocarbon species remaining in the hydrocarbon containing gas sample following the diffusion.

* * * * *